United States Patent
Rothschild et al.

(10) Patent No.: US 6,458,531 B1
(45) Date of Patent: Oct. 1, 2002

(54) LEPTIN RECEPTOR GENE AS A GENETIC MARKER FOR LEANNESS IN PIGS

(75) Inventors: Max F. Rothschild, Ames; Amy L. Vincent, Jewel, both of IA (US); Catherine W. Ernst, East Lansing, MI (US)

(73) Assignee: Iowa State University Research Foundation, Ames, IA (US)

( * ) Notice: Subject to any disclaimer, the term of this patent is extended or adjusted under 35 U.S.C. 154(b) by 0 days.

(21) Appl. No.: 08/946,800

(22) Filed: Oct. 8, 1997

Related U.S. Application Data

(60) Provisional application No. 60/028,100, filed on Oct. 9, 1996.

(51) Int. Cl.[7] .......................... C12Q 1/68; C12P 19/34; C07H 21/02; C07H 21/04
(52) U.S. Cl. .................. 435/6; 435/91.1; 435/91.2; 536/22.1; 536/23.1; 536/23.51; 536/24.33
(58) Field of Search .................. 435/6, 91.1, 91.2; 536/23.1, 23.5, 23.51, 24.31, 24.33

(56) References Cited

U.S. PATENT DOCUMENTS 5,972,621 A    10/1999 Tartaglia et al.

OTHER PUBLICATIONS

Tartaglia et al Cell vol. 83 pp. 1263–1271, 1995.*
Designer Primers NAR vol. 22, No. 15, 1994.*
Genbank Acc No. AF092422 three sheets, 1996.*
Wang et al J. of An. Sci vol. 75 No. 8 p. 2287, 1997.*
MASPAR Sequence Search Seq ID No:1 one sheet, 1998.*
MASPAR Sequence Search Seq ID No:2 one sheet, 1998.*
MASPAR Sequence Search Seq ID No:5 one sheet, 1998.*
MASPAR Sequence Search Seq ID No:6 one sheet, 1998.*
Chemical Abstract vol. 53 pp. 2624—DE 00952264.
Derwent Abstract—DE 1454824.
Derwent Abstract—DE 3032778.

* cited by examiner

*Primary Examiner*—Jeffrey Siew
(74) *Attorney, Agent, or Firm*—McKee, Voorhees & Sease, P.L.C.

(57) ABSTRACT

Disclosed herein are genetic markers for pig leanness, methods for identifying such markers, and methods of screening pigs to determine those more or less likely to be obese and more or less likely to produce litters with leans or obese offspring and preferably selecting those pigs for future breeding purposes. The markers are based upon the presence or absence of certain polymorphisms in the pig leptin receptor gene.

22 Claims, 3 Drawing Sheets

LEPTIN RECEPTOR GENE AS A GENETIC MARKER FOR LEANNESS IN PIGS

CROSS-REFERENCE TO RELATED APPLICATION

This application is a continuation-in-part of commonly owned, provisional application, U.S. Ser. No. 60/028,100 filed on Oct. 9, 1996.

FIELD OF THE INVENTION

This invention relates generally to the detection of genetic differences for leanness among pigs and particularly use of a genetic marker in the leptin receptor gene which is indicative of the heritable trait of low fat content in pigs.

BACKGROUND OF THE INVENTION

There is an increasing consumer demand for meat products having low fat content. This demand is fueled by accumulating evidence in the scientific literature that a high consumption of animal fat, especially fat with a high proportion of saturated fatty acids, represents a significant health hazard, including risk for cardiovascular disease. Other health concerns associated with high fat meats include their high content of cholesterol and the addition of relatively high amounts of salt which are added to improve the binding characteristics since salt aids in extracting the native water binding component myosin from the meat. Furthermore an increasing number of consumers find meat products containing chemical additives such as phosphates, emulsifying additives, and anti-oxidants less acceptable.

Faced with consumers who seek a healthier meat product, meat producers are continually pressed to offer cheaper and healthier products.

Genetic differences exist among individual meat producing animals as well as among breeds which can be exploited by breeding techniques to achieve animals with these desirable characteristics. Chinese breeds are known for reaching puberty at an early age and for their large litter size. American breeds are known for their greater growth rates and leanness. Thus, it would be desirable to combine the best characteristics of both types of breeds, thereby improving pork production.

Often, however heritability for desired traits is low for example heritability for litter size is around 10%–15%. Standard breeding methods which select individuals based upon phenotypic variations do take into account genetic variability or complex gene interactions which exist. Therefore, there is a need for an approach that deals with selection for reproduction at the cellular or DNA level. This method will provide a method for genetically evaluating animals to enable breeders to more accurately select those animals which not only phenotypically express desirable traits but those which express favorable underlying genetic criteria. This has largely been accomplished to date by marker assisted selection.

RFLP analysis has been used by several groups to study pig DNA. Jung et al., *Theor. Appl. Genet.*, 77:271–274 (1989), incorporated herein by reference, discloses the use of RFLP techniques to show genetic variability between two pig breeds. Polymorphism was demonstrated for swine leukocyte antigen (SLA) Class I genes in these breeds. Hoganson et al., *Abstract for Annual Meeting of Midwestern Section of the American Society of Animal Science*, Mar. 26–28, 1990, incorporated herein by reference, reports on the polymorphism of swine major histocompatibility complex (MHC) genes for Chinese pigs, also demonstrated by RFLP analysis. Jung et al. *Animal Genetics*, 26:79–91 (1989), incorporated herein by reference, reports on RFLP analysis of SLA Class I genes in certain boars. The authors state that the results suggest that there may be an association between swine SLA/MHC Class I genes and production and performance traits. They further state that the use of SLA Class I restriction fragments, as genetic markers, may have potential in the future for improving pig growth performance.

The ability to follow a specific favorable genetic allele involves the identification of a DNA molecular marker for a major effect gene. The marker may be linked to a single gene with a major effect or linked to a number of genes with additive effects. DNA markers have several advantages; segregation is easy to measure and is unambiguous, and DNA markers are co-dominant, i.e., heterozygous and homozygous animals can be distinctively identified. Once a marker system is established selection decisions could be made very easily, since DNA markers can be assayed any time after a blood sample can be collected from the individual infant animal.

The use of genetic differences in receptor genes has become a valuable marker system for selection. For example U.S. Pat. Nos. 5,550,024 and 5,374,526 to Rothschild et. al. disclose a polymorphism in the pig estrogen receptor gene which is associated with larger litter size, the disclosure of which is incorporated herein by reference. U.S. application Ser. No. 08/812,208 filed Mar. 6, 1997 now U.S. Pat. No. 5,935,784 filed Aug. 10, 1999 discloses polymorphic markers in the pig prolactin receptor gene which are associated with larger litter size and overall reproductive efficiency.

The present invention provides a genetic marker, based upon the discovery of a polymorphism in the leptin receptor gene, which relates to leanness in pigs. This will permit genetic typing of pigs for their leptin receptor genes and for determination of the relationship of specific RFLPs to leanness. It will also permit the identification of individual males and females that carry the gene for leanness. Thus, the markers may be selection tools in breeding programs to develop lines and breeds that produce litters containing offspring with less fat content.

The murine autosomal recessive mutations obese (ob), diabetes (db) and fatty (fa) were first reported in the 1960s. The phenotypes of animals homozygous for these mutations include severe, early-onset obesity, insulin resistance and susceptibility to diabetes. The ob gene has recently been cloned in human and mouse and its protein product identified as leptin. Subsequent research led to the identification of a receptor for leptin in mice (OBR). The gene for OB-R was shown to map to within a 5.1 cM interval of mouse Chr 4 which contains the db locus. This report was followed by two studies providing evidence that db was the gene encoding OB-R. A recent report by Chua and associates has confirmed that db, fa and OB-R are the same gene. The mouse leptin receptor gene has now been assigned the symbol, Lepr, which replaces the previously used symbols OB-R and Obr. Mapping of human leptin receptor gene (LEPR) has also recently been reported.

According to the invention a polymorphism was identified in the leptin receptor gene which is associated with the leaner phenotype typically seen in American breeds.

It is an object of the invention to provide a method of screening pigs to determine those more likely to produce offspring with low fat content.

Another object of the invention is to provide a method for identifying genetic markers for pig leanness.

A further object of the invention is to provide genetic markers for selection and breeding to obtain pigs that will be expected to have a lower fat content as exemplified by the American breeds.

Yet another object of the invention is to provide a kit for evaluating a sample of pig DNA for specific genetic markers of leanness.

Additional objects and advantages of the invention will be set forth in part in the description that follows, and in part will be obvious from the description, or may be learned by the practice of the invention. The objects and advantages of the invention will be attained by means of the instrumentalities and combinations particularly pointed out in the appended claims.

SUMMARY OF THE INVENTION

To achieve the objects and in accordance with the purpose of the invention, as embodied and broadly described herein, the present invention provides a method for screening pigs to determine those which will be likely to produce offspring with a lower fat content when bred or to select against pigs which have alleles indicating higher fat content. As used herein "low fat content or leanness" means an increase in leanness above the mean of a given population. Thus, the present invention provides a method for screening pigs to determine those more likely to produce low fat offspring, and/or those less likely to produce obese offspring, which method comprises the steps 1) obtaining a sample of genomic DNA from a pig; and 2) analyzing the genomic DNA obtained in 1) to determine which leptin allele(s) is/are present. Briefly, a sample of genetic material is obtained from a pig, and the sample is analyzed to determine the presence or absence of a polymorphism in the leptin receptor gene that is correlated with leanness.

In one embodiment the polymorphism is a restriction fragment length polymorphism and the assay comprises identifying the pig leptin receptor gene from isolated pig genetic material; exposing the gene to a restriction enzyme that yields restriction fragments of the gene of varying length; separating the restriction fragments to form a restriction pattern, such as by electrophoresis or HPLC separation; and comparing the resulting restriction fragment pattern from a pig leptin receptor gene that is either known to have or not to have the desired marker. If a pig tests positive for the marker, such pig can be considered for inclusion in the breeding program. If the pig does not test positive for the marker genotype the pig can be culled from the group and otherwise used.

In a most preferred embodiment the gene is isolated by the use of primers and DNA polymerase to amplify a specific region of the gene which contains the polymorphism. Next the amplified region is digested with a restriction enzyme and fragments are again separated. Visualization of the RFLP pattern is by simple staining of the fragments, or by labeling the primers or the nucleoside triphosphates used in amplification.

It is also possible to establish linkage between specific alleles of alternative DNA markers and alleles of DNA markers known to be associated with a particular gene (e.g. the leptin receptor gene discussed herein), which have previously been shown to be associated with a particular trait. Thus, in the present situation, taking the leptin receptor gene, it would be possible, at least in the short term, to select for pigs likely to produce lean litters, or alternatively against pigs likely to produce obese or high fat litters, indirectly, by selecting for certain alleles of the leptin receptor associated marker through the selection of specific alleles of alternative chromosome 6 markers. According to the invention, examples of markers on the published PiGMaP chromosome 6 map which are linked to the leptin receptor gene include S0059, S0228, S0003, S0299, S0121, SO146 and S0031. A multiple point analysis produced the best map order of these marker and LEPR (with distance in Kosambi cM): S0059-13.3-S0228-1.0-S0003-4.4-S0299-4.5-S0121-7.9-LEPR-22.1-S0146-3.3-S0031.

The invention further comprises a kit for evaluating a sample of pig DNA for the presence in pig genetic material of a desired genetic marker located in the pig leptin receptor gene indicative of the heritable trait of low body fat. At a minimum, the kit is a container with one or more reagents that identify a polymorphism either in or associated with the pig leptin receptor gene. Preferably, the reagent is a set of oligonucleotide primers capable of amplifying a fragment of the pig leptin receptor gene that contains the polymorphism. The kit further may contain a restriction enzyme that cleaves the pig leptin receptor gene in at least one place. In a most preferred embodiment the restriction enzyme is HinfI or MboI or one which cuts at the same recognition sites.

The accompanying figures, which are incorporated herein and which constitute a part of this specification, illustrates one embodiment of the invention and, together with the description, serve to explain the principles of the invention.

DETAILED DESCRIPTION OF THE INVENTION

Figure 1:
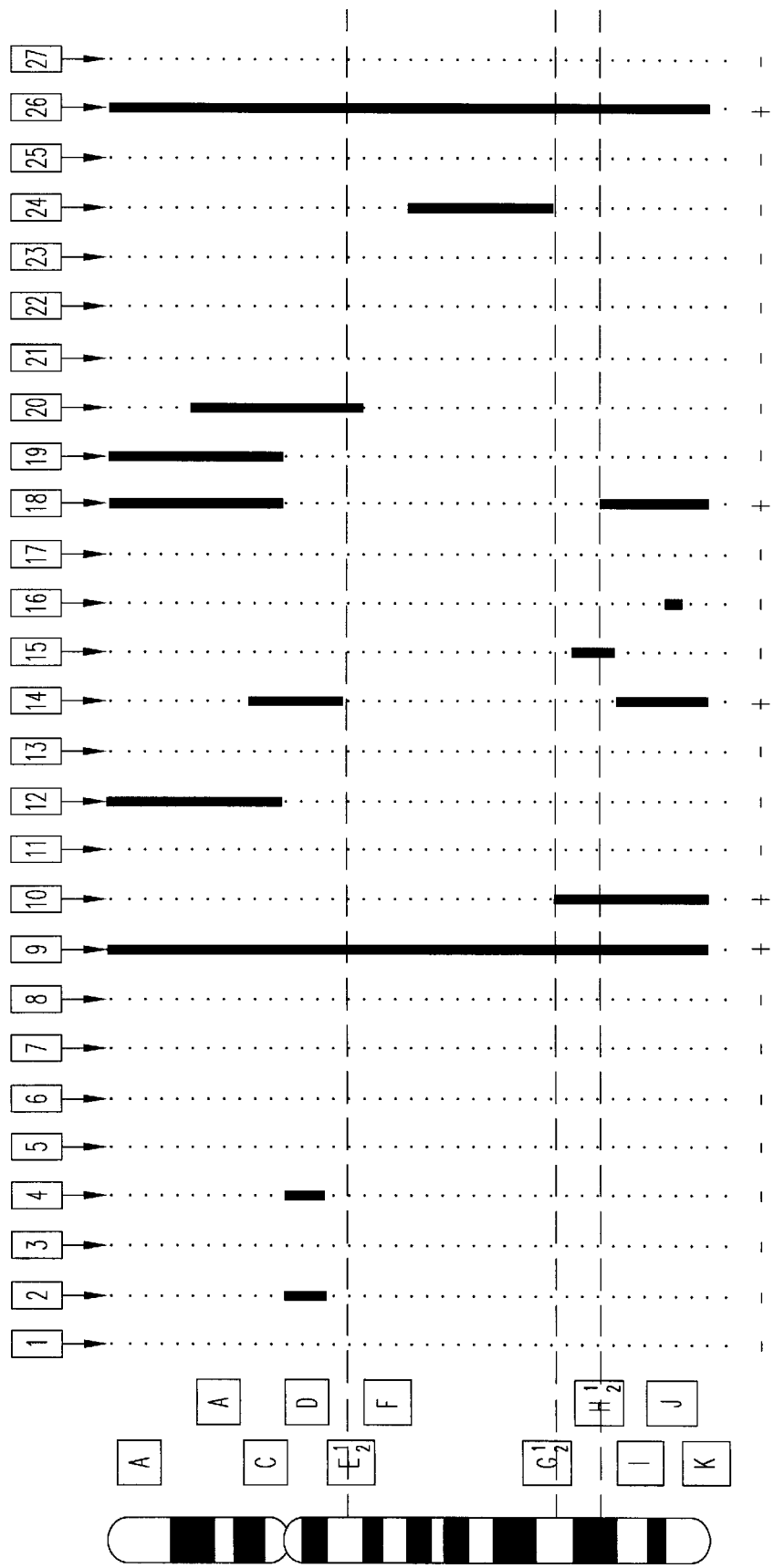
FIG. 1 is a diagram representing the presence of fragments of porcine Chr 6 in each hybrid clone. The chromosome fragments are shown as solid bars spanning the length of the fragment. The presence of various Chr 6 fragments enables the definition of regions named by a capital letter and alternatively represented in gray or white. Regions I and K were retained by the same hybrids and thus cannot be distinguished. Positive hybrids for LEPR were 9, 10, 14, 18 and 26 indicating that LEPR maps to either Region I or Region K of chromosome 6.

Reference will now be made in detail to the presently preferred embodiments of the invention, which together with the following examples, serve to explain the principles of the invention.

The invention relates to genetic markers associated with leanness in pigs. It provides a method of screening pigs to determine those more likely to produce a leaner offspring when bred by identifying the presence or absence of a polymorphism in the leptin receptor gene that is correlated with leanness. Used herein, the term "leanness" means a biologically significant decrease in body fat below the mean of a given population.

Thus, the invention relates to genetic markers and methods of identifying those markers in a pig of a particular breed, strain, population, or group, whereby the selected pig is more likely to produce a litter that is significantly above the average leanness for that particular breed, strain, population, or group. Any method of identifying the presence or absence of this marker may be used, including for example single-strand conformation polymorphism (SSCP) analysis, RFLP analysis, heteroduplex analysis, denaturing gradient gel electrophoresis, and temperature gradient electrophoresis, ligase chain reaction or even direct sequencing of the leptin receptor gene and examination for the HinfI or MboI recognition pattern.

Other possible techniques include non-gel systems such as TaqMan™ (Perkin Elmer). In this system oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete, i.e. there is a mismatch of some form, the cleavage of the dye does not take place. Thus only if the nucleotide sequence of the oligonucleotide probe is completely complementary to the template molecule to which it is bound will quenching be removed. A reaction mix can contain two different probe sequences each designed against different alleles that might be present thus allowing the detection of both alleles in one reaction.

The use of RFLPs is the preferred method of detecting the polymorphism. However, since the use of RFLP analysis depends ultimately on polymorphisms and DNA restriction sites along the nucleic acid molecule, other methods of detecting the polymorphism can also be used. Such methods include ones that analyze the polymorphic gene product and detect polymorphisms by detecting the resulting differences in the gene product.

RFLP analysis in general is a technique well-known to those skilled in the art. See, for example, U.S. Pat. No. 4,582,788 issued Apr. 15, 1986 to Erlich and U.S. Pat. No. 4,666,828 issued May 19, 1987 to Gusella, U.S. Pat. No. 4,772,549 issued Sep. 20, 1988 to Frossard, and U.S. Pat. No. 4,861,708 issued Aug. 29, 1989 to Frossard, all of which are incorporated herein by reference. Broadly speaking, the technique involves obtaining the DNA to be studied, digesting the DNA with restriction endonucleases, separating the resulting fragments, and detecting the fragments of various genes.

In the present invention, a sample of genetic material is obtained from a pig. Samples can be obtained from blood, tissue, semen, etc. Generally, peripheral blood cells are used as the source, and the genetic material is DNA. A sufficient amount of cells are obtained to provide a sufficient amount of DNA for analysis. This amount will be known or readily determinable by those skilled in the art. The DNA is isolated from the blood cells by techniques known to those skilled in the art.

Next the region containing the polymorphism is amplified by the use of primers and standard techniques, such as the polymerase chain reaction. This technique is described in U.S. Pat. No. 4,683,195, issued Jul. 28, 1987 to Mullis et al., U.S. Pat. No. 4,683,202, issued Jul. 28, 1987 to Mullis, U.S. Pat. No. 4,800,159 issued Jan. 24, 1989 to Mullis, et al., U.S. Pat. No. 4,889,818 issued Dec. 26, 1989 to Gelfand, et al., and U.S. Pat. No. 4,902,624, issued Feb. 20, 1990 to Clumbus, et al., all of which are incorporated herein by reference. The selection of primers is discussed in the references mentioned and incorporated herein. The primers should amplify the leptin receptor gene or at a minimum the portion of the leptin receptor gene which contains the polymorphic site (or one associated with it) identified herein.

The isolated DNA is then digested with a restriction endonuclease that cleaves or cuts DNA hydrolytically at a specific nucleotide sequence, called a restriction site. Such endonucleases, also called restriction enzymes, are well-known to those skilled in the art. For the present invention, one should be chosen that cleaves the pig leptin receptor gene in at least one place, producing at least two fragments of the gene. A determination is made as to whether or not any such fragments are polymorphic and if any polymorphism (RFLP) is associated with leanness by techniques known in the art in conjunction with the teachings contained herein. Preferably, the restriction endonuclease is HinfI or MboI. HinfI cuts double stranded DNA at the sequence 5'-G|ANTC-3' MboI cuts at athe |GATC. The amount of such enzyme to be added to the sample containing the pig DNA and the other appropriate conditions for treating the sample will be readily determinable to persons skilled in the art, given the teachings contained herein.

The restriction fragments are then analyzed by known techniques that generally involve either the separation of the fragments and visualization by staining or subsequent blotting and hybridization to obtain a particular pattern or the determination of different sizes of the fragments. The latter permits the identification of one or more fragments (markers) for leanness. The preferred separation technique is gel electrophoresis.

In this technique, the digested fragments are separated in a supporting medium by size under the influence of an applied electric field. Gel sheets or slabs, such as agarose or agarose-acrylamide, are typically used as the supporting medium. The sample, which contains the restriction fragments, is added to one end of the gel. One or more size markers are run on the same gel as controls to permit an estimation of the size of the restriction fragments. This procedure generally permits a degree of resolution that separates fragments that differ in size from one another by as little as 100 base pairs.

In alternative embodiments, the fragments are denatured and transferred physically from the gel onto a solid support, preferably a nylon membrane, by contacting the gel with the filter in the presence of appropriate reagents and under appropriate conditions that promote the transfer of the DNA. Such reagents and conditions are well-known to those skilled in the art. Thus, the relative positions of the DNA fragments resulting from the separation procedure are maintained.

The next step involves the detection of the various categories of sizes of the fragments or, alternatively, the detection of a fragment of a particular size. The latter may be of particular interest because it is a genetic marker associated with leanness. This is preferably accomplished via staining of the fragments with ethidium bromide or the like.

An alternative technique is the use of a hybridization probe. Such a probe is an oligonucleotide or polynucleotide that is sufficiently complementary or homologous to the fragments to hybridize with them, forming probe-fragment complexes. Preferably, the probe is a cDNA probe. The oligonucleotide or polynucleotide is labeled with a detectable entity. This permits the detection of the restriction fragments, to which the probes are hybridized. The probes are labeled by standard labeling techniques, such as with a radiolabel, enzyme label, fluorescent label, biotin-avidin label, and the like. See U.S. Pat. No. 4,711,955 issued Dec. 8, 1987 to Ward et al. and U.S. Pat. No. 4,868,103 issued Sep. 19, 1989 to Stavrianopoulos et al., both of which are incorporated herein by reference.

The probes are contacted with the nylon membrane that contains the restriction fragments for a sufficient period of time and under appropriate hybridizing conditions for the probes to hybridize to the fragments. The filter is then preferably washed to remove unbound probes and other unwanted materials.

The probe-fragment complexes, which are bound to the filter, are then detected by known techniques. For example, if the probe has been radioactively labeled ($^{32}P$), detection involves contacting the nylon membrane paper with a piece of radiosensitive film. Following an appropriate exposure period, the fragments of interest, including control fragments, are visualized.

The detection step provides a pattern, resulting from the separation of the fragments by size. Comparison of these fragments with control fragments of known size that have also been run on the same gel permits the estimation of the size of the various groups of fragments. The various polymorphisms in the pig leptin receptor gene are then determined by comparison of the patterns produced by similar analysis of DNA from a number of different pigs. For some of the individual pigs, the patterns will differ from the usual pattern produced by most of the other pigs. This will be due to one or more restriction fragment length polymorphisms, i.e., restriction fragments of a different length produced by the endonuclease that cuts the pig leptin receptor gene. This indicates different base pair sequences in such pigs.

Once a particular RFLP has been identified, i.e., a restriction fragment of a particular length, a probe to this fragment may be constructed by the use of known techniques. This permits alternative and faster formats for detecting such polymorphism. For example, once the DNA is digested, a sandwich hybridization format can be used. Such an assay is disclosed in U.S. Pat. No. 4,486,539 issued Dec. 4, 1984 to Ranki, et al., and U.S. Pat. No. 4,563,419 issued Jan. 7, 1986 to Ranki, et al., both of which are incorporated herein by reference. The sample is brought into contact with a capture probe that is immobilized on a solid carrier. The probe binds the fragment. The carrier is then washed, and a labeled detection probe is added. After additional washing, the detection probe is detected, thereby demonstrating the presence of the desired fragment.

In yet another embodiment, once the RFLP pattern has been determined or a particular polymorphic fragment has been determined, it is compared to a second, known RFLP pattern or fragment that is correlated with leanness. This second pattern or fragment has also been determined from the pig leptin receptor gene, using the same restriction endonuclease as the first and the same probe or an equivalent thereof under the same conditions.

In an alternative embodiment of the invention, the restriction fragments can be detected by solution hybridization. In this technique, the fragments are first hybridized with the probe and then separated. The separated probe-fragment complexes are then detected as discussed above. Generally, such complexes are detected on the gel without transfer to filter paper.

In a most preferred embodiment the polymorphism is detected by PCR amplification without any probe. This procedure is known to those of skill in the art and is disclosed in U.S. Pat. No. 4,795,699 entitled "DNA Polymerase" and U.S. Pat. No. 4,965,188. "Process for Amplifying, Detecting, and/or Cloning Nucleic Sequences Using a Thermostable Enzyme" both of which are incorporated herein by reference.

For this procedure primers are constructed to amplify the region in which the polymorphism lies. Accordingly primers which are preferably 4–30 bases are designed based upon the sequence surrounding the polymorphism including a forward 5', primer and a reverse or anti-sense primer 3' of the polymorphism. The primers need not be the exact complement, and substantially equivalent sequences are also acceptable. A DNA polymerase is then added such as Taq polymerase (many such polymerases are known and commercially available) in the presence of the four nucleoside triphosphates and often a buffering agent. Detection is facilitated by simple staining, such as with ethidium bromide, of separated products to detect for predicted sizes based upon the length of the region amplified. Reaction times, reagents, and design of primers are all known to those of skill in the art and are discussed in the patents incorporated herein by reference. Further PCR amplification may be used in combination with Single Strand Confirmation Polymorphism (SSCP). See Detection of Polymorphism, of Human DNA by Gel Electrophoresis as Single-Strand Conformation Polymorphisms, Orita et al, PNAS 86(8) Apr. 1989 (2766–70); and Lessa et al. Mol Ecol 2(2) p. 119–29 April 1993 "Screening Techniques for Detecting Allelic variation in DNA Sequences" which are incorporated by reference.

Although the above methods are described in terms of the use of a single restriction enzyme and a single set of primers, the methods are not so limited. One or more additional restriction enzymes and/or probes and/or primers can be used, if desired. Additional enzymes, constructed probes and primers can be determined through routine experimentation.

Genetic markers for pig leanness are determined as follows. Male and female pigs of the same breed or breed cross or derived from similar genetic lineages are grown under normal conditions. The fat content of each animal is determined. RFLP analysis of the DNA is conducted as discussed above in order to determine polymorphisms in the leptin receptor gene of each pig. The polymorphisms are then associated with the fat content of the individual animals. At least 20 and preferably at least 100 pigs are used in making these determinations.

When this analysis is conducted and the polymorphism is determined by PCR RFLP analysis using the restriction endonuclease HinfI, or MboI and amplification primers may be designed using analogous human known leptin receptor sequences, or may be designed using pig leptin receptor gene sequence data as exemplified herein or even designed from sequences obtained from linkage data from closely surrounding genes. According to the invention a set of primers have been selected which amplify a 3.8 kb fragment (forward primer 5'-GCATCCCATATCTGAACCC-3' (SEQ ID NO:1) and the reverse primer 5'-CCACTTAAACCATAGCGAATC-3' (SEQ ID NO:2)) after restriction polymorphic fragments of approximately 2100, 700, 395, 350, 240, 140, and 110 base pairs are generated. The polymorphic site is located in the 350 base pair fragment and the 350 bp fragment was designated the A allele. When this fragment is cut with HinfI, 240 and 110 bp fragments are generated and is designated the B allele. Thus a pig which is heterozygous for the HinfI fragment will exhibit a pattern of 2100, 700, 395, 350, 240, 140, and 110. A homozygote for the polymorphic cut site (B allele will exhibit a pattern of 2100, 700, 395, 240, 140, and 110, while the other homozygote (A allele) exhibits a pattern of 2100, 700, 395, 350, 240 and 140. Another set of primers were also created for a second polymorphism closely related to the first one. These primers are 5'-AAAAATAAGGATGAGATGGTG-3', SEQ ID NO:5, and 5'-GAAGGAAAGGTGTGGTGAAAT-3', SEQ ID NO:6 and when the fragment is cut with MboI the A allele contains 339 and 396 bp fragments. The B allele contains 282, 57 and 39 base pairs. The genotype associated with leanness correlates with the phenotypic trends already known to exist for breeds. American breeds which are known for leanness show a lower occurrence of the A allele. While Chinese breeds which are known for being fatter and having increased reproductive efficiency exhibit a higher occurrence of the A allele.

The reagents suitable for applying the methods of the invention may be packaged into convenient kits. The kits provide the necessary materials, packaged into suitable containers. At a minimum, the kit contains a reagent that identifies a polymorphism in the pig leptin receptor gene that is associated with an leanness. Preferably, the reagent is a PCR set (a set of primers, DNA polymerase and 4 nucleoside triphosphates) that hybridize with the pig leptin receptor gene or a fragment thereof. Preferably, the PCR set and a restriction enzyme that cleaves the pig leptin receptor gene in at least one place are included in the kit. In a particularly preferred embodiment of the invention, the forward primer is SEQ ID NO:1 and the reverse primer is SEQ ID NO:3 and the restriction enzyme is HinfI, or the primer is SEQ ID NO:5 and 6 and the enzyme is MboI. Preferably, the kit further comprises additional means, such as reagents, for detecting or measuring the detectable entity or providing a control. Other reagents used for hybridization, prehybridization, DNA extraction, visualization etc. may also be included, if desired.

The methods and materials of the invention may also be used more generally to evaluate pig DNA, genetically type individual pigs, and detect genetic differences in pigs. In particular, a sample of pig genomic DNA may be evaluated by reference to one or more controls to determine if a polymorphism in the leptin receptor gene is present. Preferably, PCR-RFLP analysis is performed with respect to the pig leptin receptor gene, and the results are compared with a control. The control is the result of a PCR-RFLP analysis of the pig leptin receptor gene of a different pig where the polymorphism of the pig leptin receptor gene is known. Similarly, the leptin receptor genotype of a pig may be determined by obtaining a sample of its genomic DNA, conducting PCR-RFLP analysis of the leptin receptor gene in the DNA, and comparing the results with a control. Again, the control is the result of PCR-RFLP analysis of the leptin receptor gene of a different pig. The results genetically type the pig by specifying the polymorphism in its leptin receptor genes. Finally, genetic differences among pigs can be detected by obtaining samples of the genomic DNA from at least two pigs, identifying the presence or absence of a polymorphism in the leptin receptor gene, and comparing the results.

These assays are useful for identifying the genetic markers relating to leanness, as discussed above, for identifying other polymorphisms in the leptin receptor gene that may be correlated with other characteristics, and for the general scientific analysis of pig genotypes and phenotypes.

The genetic markers, methods, and kits of the invention are also useful in a breeding program to improve leanness in a breed, line, or population of pigs. Continuous selection and breeding of sows that are at least heterozygous and preferably homozygous for a polymorphism associated with leanness would lead to a breed, line, or population being leaner. Thus, the markers are selection tools.

It is to be understood that the application of the teachings of the present invention to a specific problem or environment will be within the capabilities of one having ordinary skill in the art in light of the teachings contained herein. The examples of the products and processes of the present invention appear in the following examples.

EXAMPLE 1

Using human and rodent information primers were designed, and a section of the LEPR gene in the pig has been amplified. The pig LEPR gene as well as a polymorphism therein was identified.

Primers:

reverse primer 5'-CCACTTAAACCATAGCGAATC-3' (SEQ ID NO:2)

forward primer 5'-GCATCCCATATCTGAACCC-3' (SEQ ID NO:1)

PCR Conditions:

|  | 25 uL reaction |
|---|---|
| PCR Mix 1 | |
| 10 mM dNTP's (Boehringer Mannheim) | 0.875 uL |
| 20 pmol/uL forward primer | 0.375 uL |
| 20 pmol/uL reverse primer | 0.375 uL |
| dd sterile H$_2$O | 5.875 uL |
| 12.5 ng/uL DNA | 3.0 uL |
| PCR Mix 2 | |
| 10X Expand Buffer 1 (Boehringer Mannheim) | 2.5 uL |
| Expand Polymerase (Boehringer Mannheim) | 0.25 uL |
| dd sterile H$_2$O | 9.75 uL |

The reagents in PCR Mix 1 should be pipetted together and 9.5 uL of this added to each reaction tube. The template is then added, then overlaid with a drop of sterile mineral oil. Place the reaction tubes on the thermal cycler held at 80° C. Add 12.5 uL PCR Mix 2, making sure to submerge the tip beneath the oil.

Thermal Cycler Program:

1. 92° C. 2 minutes 2. 92° C. 30 seconds 3. 52° C. 30 seconds 4. 68° C. 2 minutes 5. Return to step 2 for 9 more cycles 6. 92° C. 30 seconds 7. 52° C. 30 seconds 8. 68° C. 2 minutes plus 20 seconds/cycle 9. Return to step 6 for 24 more cycles 10. 68° C. 7 minutes 11. 4° C. hold 5 uL of the PCR product plus 2 uL of 6× loading dye should be placed on a 1% agarose gel to check. Run at 120V for 30 minutes and stain with ethidium bromide. The total fragment is approximately 3.8 kb pairs.

HinfI Digestion:

| Digestion Mix (per 20 uL PCR product) | Each |
|---|---|
| 10X NE Buffer 2 (New England Biolabs) | 3.0 uL |
| 10U/uL HinfI (New England Biolabs) | 0.2 uL |
| dd sterile H$_2$O | 6.8 uL |

Mix the reagents and add 10 uL to each tube. Incubate the samples at 37° C. overnight.

Figure 2:
FIG. 2 is a depiction of the fragments pattern observed for the A and B alleles.
Figure 2:
Figure 2:
Figure 3:
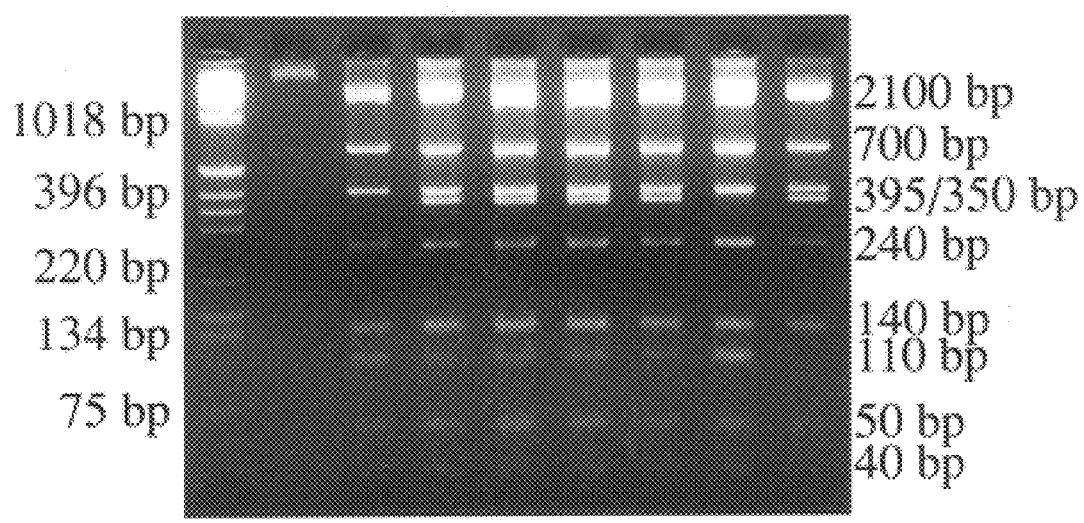
FIG. 3 is a HinfI PCR-RFLP in the porcine leptin receptor gene fragments. Lane 1: 1-kb ladder (Promega); lane 2: uncut PCR product; lane 3: BB grandsire; lane 4: AB granddam; lane 5: AB sire; lane 6: AB dam; lane 7: AB offspring; lane 8: BB offspring; lane 9: AA offspring.

Gel Electrophoresis:

The fragments are separated by loading the digest product plus 6 uL 6× loading dye on a 3% NuSieve (FMC) agarose gel at 130 volts for 45 minutes at room temperature. Stain gels with ethidium bromide. The fragment sizes of the PCR-RFLP are approximately 2.0 kb, 700 bp, 395 bp, 350 bp, 240 bp, 130 bp, 50 bp, and 40 bp with the polymorphic site being located in the 340 base pair fragment. When the polymorphic cut site is present a 110 base pair fragment is produced. A Diagram of the fragments produced is shown in FIG. 2.

Initial genotyping has shown the following gene frequencies.

TABLE 1

Allele frequencies of the HinfI polymorphism in the LEPR gene in 8 breeds of pigs.

| Breed | A | B |
|---|---|---|
| Hampshire n = 14 | 0.18 | 0.82 |
| Landrace n = 13 | o.11 | 0.89 |
| Duroc n = 12 | 0.17 | 0.83 |
| Large White n = 11 | 0.09 | 0.91 |
| Stress n = 9 | 0.17 | 0.83 |
| Meishan n = 14 | 0.75 | 0.25 |
| Berkshire n = 4 | 0.38 | 0.62 |
| Chester White n = 8 | 0.56 | 0.44 |

These gene frequencies differ by the breeds suggesting that this is a very useful marker for fatness. This is of special interest for use in lines being developed with Meishan breeding.

EXAMPLE 2

Species: Pig
Locus Name: Leptin receptor
Locus Symbol: LEPR
Map Position: 6q3.3–q3.5
Method of Mapping: Somatic cell hybrid panel
Database Deposit Information: GenBank accession number U72070
Molecular Reagents: Oligonucleotide primers designed from human CDNA sequence (GenBank accession number U43168) were used to amplify a 380-bp fragment of the porcine LEPR gene. Identity of the porcine product was confirmed by sequencing and it was found to include a 166-bp intron. Sequence similarity between human cDNA and porcine exonic sequences was 93.7%. The sequences of the primers used were: forward primer, 5'-CCAAACCTCGAGGAAAGTTTACC-3' SEQ ID NO:3; and reverse primer, 5'-AGGCTGCTCCTATGATACCTCAA-3' SEQ ID NO:4. PCR was performed using 10–50 ng genomic DNA in 30 μl reactions containing 1×PCR buffer (Perkin-Elmer), 1.5 mM MgCl$_2$, 200 μM each dNTP, 0.3 μM each primer and 1 U AmpliTaq Gold™ (Perkin-Elmer). The PCR profile included an initial denaturation of 5 minutes at 95° C. followed by 50 cycles of 95° C. for 45 seconds, 50° C. for 45 seconds, 72° C. for 1 minute and a final extension of 72° C. for 5 minutes. No PCR products were obtained from mouse or Chinese hamster genomic DNA using these reaction conditions. Analysis of 27 porcine-rodent somatic cell hybrids using the LEPR primers allowed regional assignment of LEPR to porcine Chromosome (Chr) 6q3.3–3.5 with a concordance of 100%. Positive LEPR signals were obtained for hybrids 9, 10, 14, 18 and 26 which are common only to regions I and K of Chr 6 as reported by Yerle and associates and shown in FIG. 1. Region I corresponds to 6q3.3–3.4 and region K corresponds to the distal half of 6q3.5.

Previously Identified Homologs: Human LEPR has been localized to Chr 1p32, mouse Lepr maps to Chr 4 and rat Lepr maps to Chr 5.

The assignment of LEPR to porcine Chr 6q3.3–3.5 is in agreement with the previous assignment of this gene to human Chr 1p32 since bidirectional chromosome painting analysis has demonstrated correspondence between these human and porcine chromosomal segments. This information extends the comparative mapping information for LEPR since it has also been mapped to homologous segments of mouse Chr 4 and rat Chr 5.

EXAMPLE 3

RAPID COMMUNICATION: A RESTRICTION FRAGMENT LENGTH POLYMORPHISM IN THE PORCINE LEPTIN RECEPTOR (LEPR) GENE

Polymorphism. A HinfI PCR-RFLP was identified in the porcine leptin receptor(LEPR) gene.

Source and Description of Primers. Human cDNA (GenBank accession no. U43168) sequence was used to design primers to amplify porcine genomic DNA.

Primer Sequences. Forward primer: 5'-GCATCCCATATCTGAACCC-3' (SEQ ID NO:1)

Reverse primer: 5'-CCACTTAAACCATAGCGAATC-3' (SEQ ID NO:2).

Method of Detection. The PCR amplification (25 μL final volume) was performed using 37.5 ng of genomic DNA, 350 μM each dNTP, 0.3 μM each primer, 1×Expand Buffer 1, and 0.7 unit Expand Polymerase (Boehringer Mannheim). The thermal cycler profile was 92° C. for 2 minutes; 10 cycles of 92° C. for 30 seconds, 53° C. for 30 seconds, and 68° C. for 2 minutes; then 25 cycles of 92° C. for 30 seconds, 53° C. for 30 seconds, and 68° C. for 2 minutes plus 20 seconds per cycle; followed by a final extension at 68° C. for 7 minutes. Twenty microliters of the 3.8-kb product was digested with HinfI and separated on a 3% NuSieve gel (FMC).

Description of Polymorphism. Bands of approximately 2,100, 700, 395, 350, 240, 140, and 110 bp were produced. The 350-bp fragment was designated as the A allele. When this fragment was cut with HinfI, 240- and 110-bp fragments were generated and were designated as the B allele.

Inheritance Pattern. The LEPR HinFI polymorphism was observed to have a Mendelian inheritance pattern in six three-generation families of the PiGMaP reference family (Archibald et al., 1995).

TABLE 3

Frequencies for the A allele

| Breed | A |
|---|---|
| Hampshire n = 14 | 0.18 |
| Landrace n = 13 | 0.11 |
| Duroc n = 12 | 0.17 |

TABLE 3-continued

Frequencies for the A allele

| Breed | A |
|---|---|
| Large White n = 11 | 0.09 |
| Meishan n = 14 | 0.75 |
| Berkshire n = 4 | 0.38 |
| Chester White n = 8 | 0.56 |

Chromosomal Location. The LEPR was significantly linked to seven markers on the published PiGMaP chromosome 6 map (recombination fraction and LOD score in parentheses): S0059 (0.24, 6.41), S0228 (0.15, 12.86), S003 (0.13, 9.25), S0299 (0.05, 11.03), S0121 (0.07, 19.33), S0146 (0.11, 4.29), and S0031 (0.24, 4.16). A multiple-point analysis produced the best map order of these markers and LEPR (with distance in Kosambi cM): S0059-13.3-S0028-1.0-S0003-4.4-S0299-4.5-S0121-7.9-LEPR-22.1-S0146-3.3-S0031.

Comments. The end of the pig PCR product were sequenced to confirm the product was LEPR. The coding portion of the 5' and 3' ends had 93% and 90% identities at the amino acid level, respectively, to the corresponding regions of the human sequence. The LEPR is the high-affinity receptor for leptin, a hormone secreted by adipose tissue that regulates fat deposition and satiety. Mutations in LEPR have been associated with obesity in mice (db/db) and rats (fa/fa) (Chen et al., 1996; Phillips et al., 1996).

EXAMPLE 4

An additional polymorphism was identified in exon 20 of LEPR. A limited number of animals have been genotyped with this marker and it is closely linked to the previous marker.

Forward: 5'-AAAAATAAGGATGAGATGGTG-3' (SEQ ID NO:5)
Reverse: 5'-GAAGGAAAGGTGTGGTGAAAT-3' (SEQ ID NO:6)

1. 92° C. 2 minutes
2. 92° C. 45 seconds
3. 59° C. 1 minute
4. 72° C. 45 seconds
5. Return to step 2 34 times
6. 72° C. 5 minutes
7. 4° C. hold The uncut PCR product is 378 bp. When cut with MboI, the A allele contains 339 bp and 39 bp fragments. The B-allele contains 282 bp, 57 bp, and 39 bp fragments.

REFERENCES:

Arden, K. C., Boutin, J. M., Djiane, J., Kelly, P. A., Cavenee, W. K. (1990). "The Receptors for Prolactin and Growth Hormone are Localized in the same Region of Human Chromosome 5", *Cytogenet. Cell Genet* 53:161–165.

Barinaga, M. (1996). "Researchers Nail Down Leptin Receptor", *Science* 271:913.

Bray, G. A., York, D. A. (1978). *Physiol. Rev.* 59, 719–809.

Chen, H., Charlat, O., Tartaglia, L. A., Woolf, E. A., Weng, X., Ellis, S. J., Lakey, N. D., Culpepper, J., Moore, K. J., Breitbart, R. E., Duyk, G. M., Tepper, R. I., Morgenstern, J. P. (1995). "Evidence that the diabetes gene encodes the leptin receptor: Identification of a mutation in the leptin receptor gene in db/db mice", *Cell* 84, 491–495.

Chevalet, C., Gouzy, J., SanCristobal-Gaudy, M. (1996). CABIOS. In Press.

Chua, S. C., Jr., Chung, W. K., Wu-Peng, X. S., Zhang, Y., Liu, S.-M., Tartaglia, L., Leibel; R. L. (1996). *Science* 271, 994–996.

Chung, W. K., Powerkehoe, L., Chua, M., Leibel, R. L. (1996). *Genome Res.* 6, 431–438.

Cioffi, J. A., Shafer, A. W., Zupancic, T. J., Smith-Gbur, J., Mikhail, A., Platika, D., Snodgrass, H. R. (1996). *Nature Med.* 2, 585–589.

Cybulsky, M. I., Fries, J. W. U., Williams, A. J., Sultan, P., Eddy, R., Byers, M., Shows, T., Gimbrone, M. A. Jr., Collins, T. (1991). "Gene Structure, Chromosomal Location, and Basis for Alternative mRNA Splicing of the Human VCAM1 Gene". *Proc. Nat. Acad. Sci.* 88:7859–7863.

Goureau, A., Yerle, M., Schmitz, A., Riquet, J., Milan, D., Pinton, P., Frelat, G., Gellin, J. (1996). *Genomics.* In Press.

Helm, J., Schmitz, C. B., Tuggle, C. K., Rothschild, M. F. (1994) "Rapid Communication: SacI Restriction Fragment Length Polymorphism with a Porcine Vascular Cell Adhesion Molecule 1 (VCAM1) cDNA Fragment", *J. Anim. Science* 72:2764.

Lee, G. H., Proenca, R., Montez, J. M., Carroll, K. M., Darvishzadeh, J. G., Lee, J. I., Friedman:, J. M. (1996). *Nature* 379, 632–635.

Messer, L., Wang, L., Ollivier, L., Legault, C., Rothschild, M. F., (1996a) "Mapping and Investigation of Candidate Genes for Litter Size in French Large White Pigs" *ISAG Proceedings* (submitted)

Messer, L., Wang, L., Yelich, J., Pomp, D., Geisert, R., Rothschild, M. F. (1996b) "Linkage Mapping of the Retinoic Acid Receptor Gamma (RARG) Gene to Porcine Chromosome 5". *Anim. Genet.* (in press)

Messer, L., Wang, L., Yelich, J., Pomp, D., Geisert, R., Rothschild, M. F. (1966c) "Linkage mapping of the Retinol Binding Protein 4 (RBP4) Gene to Porcine Chromosome 14". *Mammal. Genome* (in press)

Paszek, A., Wilkie, P. J., Flickinger, G. H., Beattie, C., Rohrer, G., Alexander, L. J., Wheeler, M., Schook, L. (1996) "Genomic Scan for Quantitative Trait Loci in Swine." *Proceed. Midwest. ASAS Meeting* pg. 24.

Phillips, M., Liu, Q., Hammond, H., Dugan, V., Hey, P., Caskey, C., Hess, J. (1996) "Leptin Receptor Missense Mutation in the Fatty Zucker Rat", *Nature Genetics* 13:18–19.

Robic, A., Riquet, J., Yerle, M., Milan, D., Lahbib-Mansais, Y., Dubut-Fontana, C., Gellin, J. (1996). *Mamm. Genome* 7, 438–445.

Rothschild, M. F., Jacobson, C., Vaske, D. A., Tuggle, C. K., Wang, L., Short, T. H., Erchardt, G. R., Sasaki, S., Vincent, A., McLaren, D. G., Southwood, O., van der Steen, H., Mileham, A., Plastow, G. (1996). "The Estrogen Receptor Locus is Associated With a Major Gene for Litter Size in Pigs". *PNAS* 93: 201–205.

Tartaglia, L. A., Dembski, M., Weng, X., Deng, N., Culpepper, J., Devos, R., Richards, G. J., Campfield, L. A., Clark, F. T., Deeds, J., Muir, C., Sander, S., Moriarty, A., Moore, K. J., Smutko, J. S., Mays, G. G., Woolf, E. A., Selent-Munro, C., Tepper, R. I. (1995) "Identification and Expression Cloning of a Leptin Receptor (OB-R)" *Cell* 83:1263–1271

Truett, G. E., Jacob, H. J., Miller, J., Drouin, G., Bahary, N., Smoller, J. W., Lander, E. S., Leibel, R. L. (1995). *Mamm. Genome* 6, 25–30.

Warner, C. M., Rothschild, M. F. (1991). "The Swine Major Histocompatibility Complex (SLA)" in *Immunogenetics of the MHC*, VCH Publishers, NY., N.Y. pp. 368–397.

Winick, J. D., Stoffel, M., Friedman, J. M. (1996). *Genomics* 36, 221–222.

Xy, Y., Jim, P., Mellor, A. L., Warner, C. M. (1994) "Identification of the Ped Gene at the Molecular Level: The Q9 MHC Class I Transgene Converts the Ped Slow Phenotype to Ped Fast Phenotype" *Biol. Reprod.* 51:695–699.

Yerle, M., Erchard, G., Robic, A., Mairal, A., Dubut-Fontana, C., Riquet, J., Pinton, P., Milan, D., Lahbib-Mansais, Y., Gellin, J. (1996). *Cytogenet. Cell Genet.* 73, 194–202.

Youngs, C. R., Ford, S. P., McGinnis, L. K., Anderson, L. H. (1993) "Investigation into the Control of Litter Size in Swine: I. Comparative Studies on in vitro Development of Meishan and Yorkshire Preimplantation Embryos" *J. Anim. Sci.*, 1561–1565.

Zhang, Y., Proenca, P., Maffei, M., Barone, M., Leopold, L., Friedman, J. M. (1994). *Nature* 372, 425–432.

What is claimed is:

1. A method of screening pigs to determine those more likely to produce leaner offspring comprising: obtaining a sample of genetic material from a pig; and assaying for the presence of a polymorphism in the leptin receptor gene, in said sample, which is associated with leanness, and is located on chromosome 6 thereby determining those more likely to produce leaner offspring wherein the polymorphism is identifiable by a amplification by a set of primers selected from the group consisting of the set of a forward primer SEQ ID NO: 1 and reverse primer SEQ ID NO: 2 and the set of a forward primer SEQ ID NO: 5 and reverse primer SEQ ID NO: 6.

2. The method of claim 1 wherein said method of identifying the presence or absence of a polymorphism is selected from a group consisting of: restriction fragment length polymorphism (RFLP) analysis, heteroduplex analysis, single strand conformational polymorphism (SSCP), denaturing gradient gel electrophoresis (DGGE), and temperature gradient gel electrophoresis (TGGE).

3. The method of claim 1 wherein said step of assaying for the presence of said polymorphism comprises the steps of:

digesting said genetic material with a restriction enzyme that cleaves the pig leptin receptor gene in at least one place;

separating the fragments obtained from said digestion;

detecting a restriction pattern generated by said fragments; and comparing said pattern with a second restriction pattern for the pig leptin receptor gene obtained by using said restriction enzyme, wherein said second restriction pattern is associated with leanness.

4. The method of claim 3 wherein said restriction enzyme is HinfI.

5. The method of claim 3 wherein said restriction enzyme is MboI.

6. The method of claim 3 wherein said separation is by gel electrophoresis.

7. The method of claim 3 wherein said step of comparing said restriction patterns comprises identifying specific fragments by size and comparing the sizes of said fragments.

8. The method of claim 3 further comprising the step of amplifying the pig leptin receptor gene or a portion thereof which contains said polymorphism, prior to said digestion step.

9. The method of claim 3 wherein said polymorphism is a polymorphic HinfI restriction site.

10. The method of claim 3 wherein said polymorphism is a polymorphic MboI restriction site.

11. The method of claim 8 wherein said pig leptin receptor gene is located on chromosome 6.

12. The method of claim 1 wherein said amplification includes the steps of:

selecting a forward and reverse sequence primer capable of amplifying a region pig leptin receptor gene which contains a polymorphic HinfI site.

13. The method of claim 1 wherein said amplification includes the steps of:

selecting a forward and a reverse sequence primer capable of amplifying a region pig leptin receptor gene which contains a polymorphic MboI site.

14. The method of claim 12 wherein said forward and reverse primers amplify the region on chromosome 6 associated with the pig leptin receptor gene.

15. The method of claim 12 wherein said forward and reverse primers amplify a polymorphism found in exon 20 of the leptin receptor gene.

16. The method of claim 14 wherein said primers are SEQ ID NO:1 and SEQ ID NO:2.

17. The method of claim 13 wherein said primer set comprise SEQ ID NO:5 and SEQ ID NO:6.

18. A method for identifying a polymorphism for pig leanness comprising the steps of:

determining the leanness of each animal; determining the polymorphism in the leptin receptor gene of each pig wherein the polymorphism is identifiable by amplification by a set of primers selected from the group consisting of the set of a forward primer SEQ ID NO: 1 and reverse primer SEQ ID NO: 2 and the set of a forward primer SEQ ID NO: 5 and reverse primer SEQ ID NO: 6; and associating the number of leanness of each pig with said polymorphism thereby identifying a polymorphism for pig leanness.

19. The method of claim 18 further comprising the step of:

selecting pigs for breeding which are predicted to have leanness by said marker.

20. The method of claim 15 wherein said analysis comprises digestion of PCR amplified DNA with the restriction enzyme HinfI.

21. The method of claim 8 wherein said polymorphism associated with leanness is amplified by use of first and second primers comprising at least 4 consecutive bases in SEQ ID NOS: 1 and 2 or 5 and 6.

22. A method for determining the presence of a polymorphic site in the leptin receptor gene which is associated with increased leanness in pigs comprising: obtaining genetic samples from male and female pigs of the same breed, or breed cross, or derived from similar genetic lineages grown under normal conditions;

determining fat content of each pig from which a genetic sample was obtained;

analyzing the genetic samples for polymorphisms in a gene associated with fat deposition wherein the gene is the leptin receptor gene wherein the polymorphisms are identifiable by amplification by a set of primers selected from the group consisting of the set of a forward primer SEQ ID NO: 1 and reverse primer SEQ ID NO: 2 and the set of a forward primer SEQ ID NO: 5 and reverse primer SEQ ID NO: 6; and correlating the polymorphism(s) to leanness by comparing the presence of polymorphisms to fat content.

* * * * *

SEQUENCE LISTING

```
<160> NUMBER OF SEQ ID NOS: 6

<210> SEQ ID NO 1
<211> LENGTH: 19
<212> TYPE: DNA
<213> ORGANISM: Porcine

<400> SEQUENCE: 1
gcatcccata tctgaaccc                                            19

<210> SEQ ID NO 2
<211> LENGTH: 21
<212> TYPE: DNA
<213> ORGANISM: Porcine

<400> SEQUENCE: 2
ccacttaaac catagcgaat c                                         21

<210> SEQ ID NO 3
<211> LENGTH: 23
<212> TYPE: DNA
<213> ORGANISM: Porcine

<400> SEQUENCE: 3
ccaaacctcg aggaaagttt acc                                       23

<210> SEQ ID NO 4
<211> LENGTH: 23
<212> TYPE: DNA
<213> ORGANISM: Porcine

<400> SEQUENCE: 4
aggctgctcc tatgatacct caa                                       23

<210> SEQ ID NO 5
<211> LENGTH: 21
<212> TYPE: DNA
<213> ORGANISM: Porcine

<400> SEQUENCE: 5
aaaaataagg atgagatggt g                                         21

<210> SEQ ID NO 6
<211> LENGTH: 21
<212> TYPE: DNA
<213> ORGANISM: Porcine
```

```
<400> SEQUENCE: 6
gaaggaaagg tgtggtgaaa t                                          21
```